United States Patent [19]

Cheney, II et al.

[11] Patent Number: 5,568,806
[45] Date of Patent: Oct. 29, 1996

[54] TRANSCUTANEOUS SENSOR INSERTION SET

[75] Inventors: Paul S. Cheney, II, Beverly Hills; John J. Mastrototaro, Los Angeles; Nannette M. Schnabel; Peter C. Lord, both of Valencia; William P. Van Antwerp, Los Angeles; Raymond D. Clark, Valencia, all of Calif.

[73] Assignee: MiniMed Inc., Sylmar, Calif.

[21] Appl. No.: 393,159

[22] Filed: Feb. 16, 1995

[51] Int. Cl.⁶ .................................................. A61B 5/00
[52] U.S. Cl. .................................. 128/635; 128/632
[58] Field of Search .................................. 128/632, 634, 128/635, 637, 639–642, 644, 917, 919, DIG. 26; 604/49, 51, 52, 158, 160–164, 174, 180

[56]  References Cited

U.S. PATENT DOCUMENTS

| | | |
|---|---|---|
| 3,399,674 | 9/1968 | Pannier et al. . |
| 3,878,830 | 4/1975 | Bicher . |
| 4,141,365 | 2/1979 | Fischeli et al. . |
| 4,562,751 | 1/1986 | Nason et al. . |
| 4,573,994 | 3/1986 | Fischell et al. . |
| 4,678,408 | 7/1987 | Nason et al. . |
| 4,685,903 | 8/1987 | Cable et al. . |
| 4,953,552 | 9/1990 | DeMarzo . |
| 5,071,408 | 12/1991 | Ahmed . |
| 5,108,819 | 4/1992 | Heller et al. . |
| 5,299,571 | 4/1994 | Mastrototaro . |

*Primary Examiner*—Angela D. Sykes
*Assistant Examiner*—Samuel Gilbert
*Attorney, Agent, or Firm*—Kelly Bauersfeld & Lowry

[57]  ABSTRACT

An improved insertion set is provided for transcutaneous placement of a sensor such as a glucose sensor at a selected site within the body of a patient. The insertion set comprises an insertion needle extending through a mounting base adapted for mounting onto the patient's skin. A flexible thin film sensor includes a proximal segment carried by the mounting base and adapted for electrical connection to a suitable monitor or the like, and a distal segment protruding from the mounting base with sensor electrodes thereon for transcutaneous placement. The distal segment of the sensor and a distal segment of the insertion needle are positioned within a flexible cannula which extends from the mounting base, whereby placement of the mounting base onto the patient's skin causes the insertion needle to pierce the skin for transcutaneous placement of the cannula with the sensor therein. The insertion needle can then be withdrawn from the cannula and the mounting base to leave the sensor distal segment at the selected insertion position, with the sensor electrodes being exposed to patient blood or other extracellular fluid via a window formed in the cannula. The cannula is carried by the mounting base to insure alignment of the sensor electrodes with the cannula window.

18 Claims, 2 Drawing Sheets

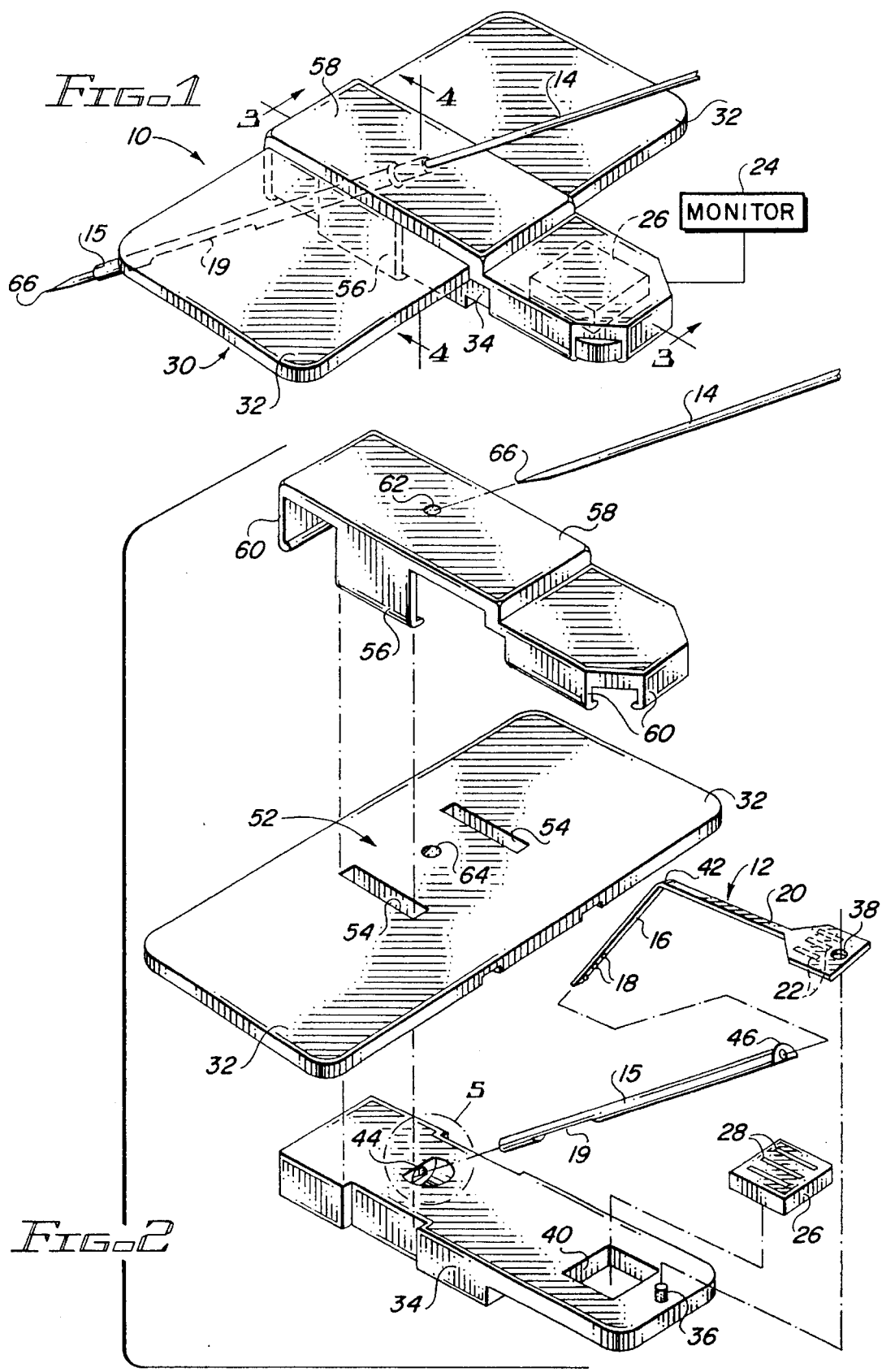

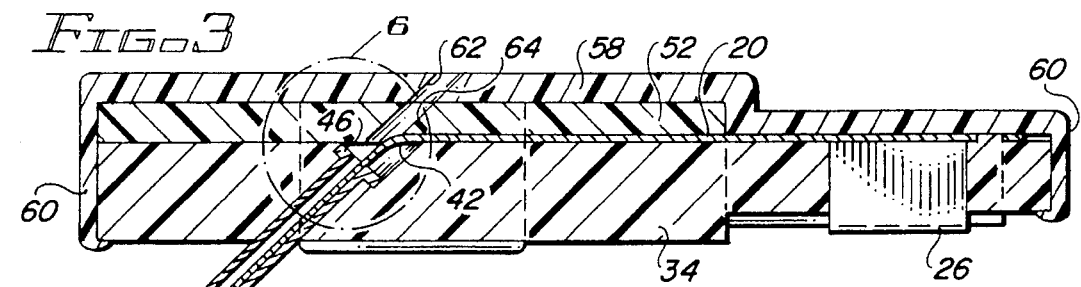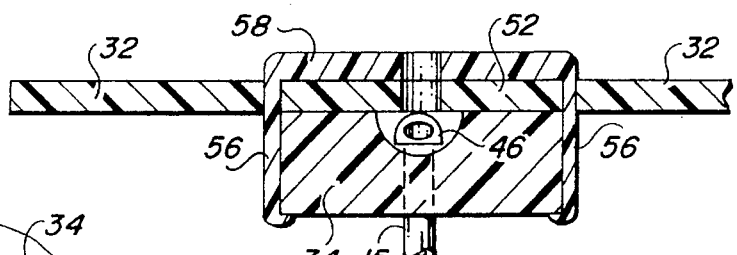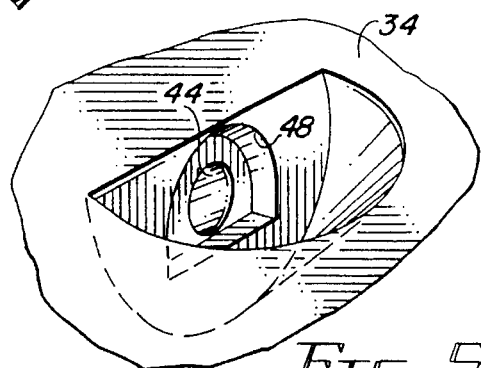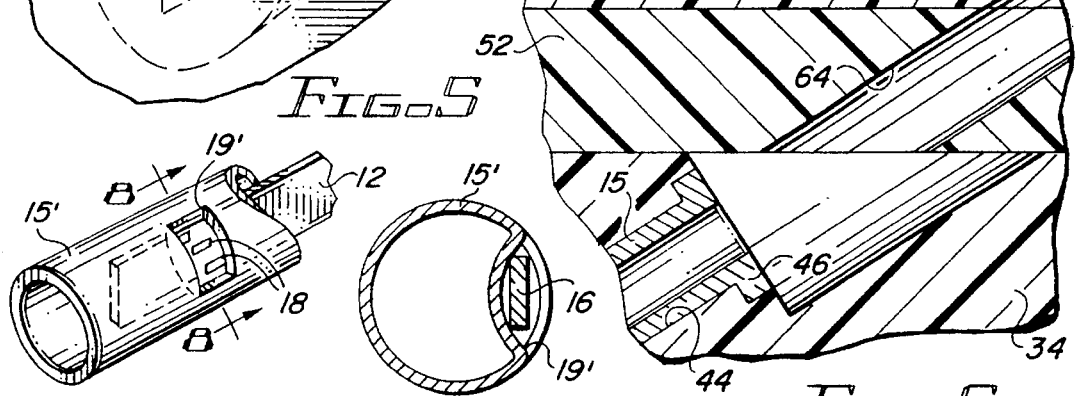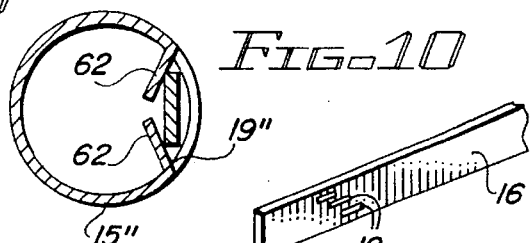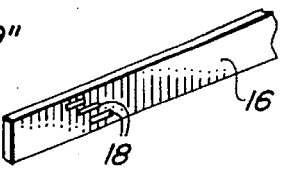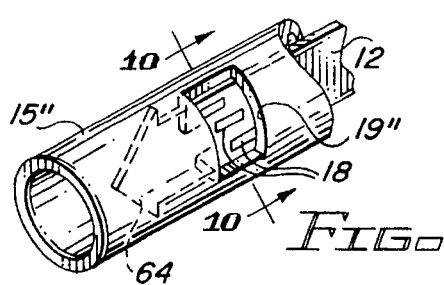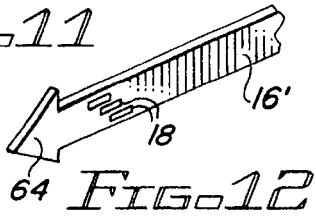

TRANSCUTANEOUS SENSOR INSERTION SET

BACKGROUND OF THE INVENTION

This invention relates generally to devices and methods for placing a sensor at a selected site within the body of a patient. More specifically, this invention relates to an improved and relatively simple insertion set for quick and easy transcutaneous placement of a flexible thin film sensor of the type used, for example, to obtain periodic blood glucose readings.

In recent years, a variety of electrochemical sensors have been developed for a range of applications, including medical applications for detecting and/or quantifying specific agents in a patient's blood. As one example, glucose sensors have been developed for use in obtaining an indication of blood glucose levels in a diabetic patient. Such readings can be especially useful in monitoring and/or adjusting a treatment regimen which typically includes regular administration of insulin to the patient. In this regard, blood glucose readings are particularly useful in conjunction with semiautomated medication infusion pumps of the external type, as generally described in U.S. Pat. Nos. 4,562,751; 4,678,408; and 4,685,903; or automated implantable medication infusion pumps, as generally described in U.S. Pat. No. 4,573,994.

Relatively small and flexible electrochemical sensors have been developed for subcutaneous placement of sensor electrodes in direct contact with patient blood or other extracellular fluid, wherein such sensors can be used to obtain periodic readings over an extended period of time. In one form, flexible transcutaneous sensors are constructed in accordance with thin film mask techniques wherein an elongated sensor includes thin film conductive elements encased between flexible insulative layers of polyimide sheet or similar material. Such thin film sensors typically include exposed electrodes at a distal end for transcutaneous placement in direct contact with patient blood or the like, and exposed conductive contacts at an externally located proximal end for convenient electrical connection with a suitable monitor device. Such thin film sensors hold significant promise in patient monitoring applications, but unfortunately have been difficult to place transcutaneously with the sensor electrodes in direct contact with patient blood or other extracellular fluid. Improved thin film sensors and related insertion sets are described in commonly assigned copending U.S. Ser. Nos. 08/213,101, filed Mar. 14, 1994, now U.S. Pat. Nos. 5,390,671; 08/212,961, filed Mar. 14, 1994 now U.S. Pat. Nos. 5,391,950; and 08/239,960 now U.S. Pat. No. 5,482,473, filed May 9, 1994, which are incorporated by reference herein. See also U.S. Pat. No. 5,299,571.

The present invention relates specifically to an improved sensor insertion set adapted for quickly and easily placing a thin film sensor on a patient with sensor electrodes in direct contact with patient blood or other extracellular fluid.

SUMMARY OF THE INVENTION

In accordance with the invention, a subcutaneous insertion set is provided for placing a flexible sensor such as a thin film electrochemical sensor at a selected site within the body of a patient. The insertion set comprises an insertion needle extending through a mounting base adapted for seated mounting onto the patient's skin. A flexible thin film sensor includes a proximal segment carried by the mounting base, and a distal segment protruding from the mounting base and having sensor electrodes thereon. The distal segment of the sensor and a distal segment of the insertion needle are carried within a hollow flexible cannula extending from the mounting base. When the mounting base is pressed onto the patient's skin, the insertion needle pierces the skin for transcutaneous placement of the cannula with the sensor therein. The insertion needle can then be withdrawn from the mounting base, leaving the sensor distal segment with the electrodes thereon exposed through a window or windows in the cannula for direct contact with patient fluid at the selected position within the patient, such as a subcutaneous, intravascular, intramuscular, or intravenous site. Conductive contacts on the sensor proximal end can be electrically connected to a suitable monitor device so that appropriate blood chemistry readings can be taken and monitored.

In one aspect of the invention, the cannula includes structural means which cooperates with the mounting base and/or the sensor distal segment to insure alignment of the sensor electrodes with the cannula window. More particularly, in the preferred form, a mounting flange at an upper end thereof, having a noncircular cross sectional shape such as a D-shaped cross section, for seated mounting within a matingly shaped recess formed in the mounting base. With this construction, the cannula is rotationally oriented relative to the mounting base in a predetermined manner, such that the window or windows therein are also oriented in a predetermined manner for proper alignment with the sensor electrodes. The distal segment of the sensor comprises a thin film strip fitted within the cannula to lie against or adjacent an interior wall of the cannula with the sensor electrodes exposed preferably in a generally downward direction, through the cannula window.

The insertion needle, when assembled with the mounting base to extend through the hollow cannula, supports the sensor distal segment in a position pressed against the cannula wall during transcutaneous sensor placement. After withdrawal of the insertion needle, the cannula protects the sensor to maintain the position thereof within the patient. In addition, in one embodiment, the cannula provides a transcutaneous path for delivery of fluid to or withdrawal of fluid from the patient.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a perspective view illustrating an upper side of a transcutaneous sensor insertion set embodying the novel features of the invention;

FIG. 2 is an exploded perspective view showing the transcutaneous sensor insertion set of FIG. 1;

FIG. 3 is an enlarged fragmented longitudinal section taken generally on the line 3—3 of FIG. 1;

FIG. 4 is an enlarged fragmented transverse section taken generally on the line 4—4 of FIG. 1;

FIG. 5 is an enlarged fragmented perspective view showing a portion of a mounting base for the sensor insertion set;

FIG. 6 is an enlarged fragmented sectional view corresponding generally with the encircled region 6 of FIG. 3;

FIG. 7 is a fragmented prospective view showing one alternative preferred form of the invention;

FIG. 8 is a transverse section taken generally on the line 8—8 of FIG. 7;

FIG. 9 is a fragmented perspective view showing another alternative preferred form of the invention;

FIG. 10 is a transverse section taken generally on the line 10—10 of FIG. 9;

FIG. 11 is a fragmented perspective view of a portion of a thin film sensor shown in FIGS. 7 and 8; and FIG. 12 is a fragmented perspective view of a portion of an alternative style thin film sensor shown in FIGS. 9 and 10.

DETAILED DESCRIPTION OF THE PREFERRED EMBODIMENTS

As shown in the exemplary drawings, an improved sensor insertion set referred to generally in FIG. 1 by the reference numeral 10 is provided for transcutaneous placement of a flexible sensor 12 (FIG. 2) at a selected site within the body of a patient. The insertion set 10 includes a rigid insertion needle 14 for quick and easy transcutaneous placement of a flexible hollow cannula 15 with a distal segment 16 of the sensor 12 therein, wherein the distal segment 16 has one or more sensor electrodes 18 exposed to patient fluid through a window 19 in the cannula 15. The insertion needle 14 is then withdrawable to leave the sensor distal segment 16 with electrodes 18 thereon in place within the cannula 15, at the selected insertion site.

The transcutaneous sensor insertion set 10 of the present invention is particularly designed for facilitating accurate placement of a flexible thin film electrochemical sensor of the type used for monitoring specific blood parameters representative of patient condition. The insertion set 10 is designed to place the sensor subcutaneously or at another selected site within the body of a patient, in a manner minimizing patient discomfort and trauma. In one preferred application, the sensor 12 may be designed to monitor blood glucose levels, and may be used in conjunction with automated or semiautomated medication infusion pumps of the external or implantable type as described in U.S. Pat. Nos. 4,562,751; 4,678,408; 4,685,903 or 4,573,994, to deliver insulin to a diabetic patient.

As shown best in FIGS. 2 and 3, the flexible electrochemical sensor 12 is a thin film sensor which may be constructed according to so-called thin film mask techniques to include elongated thin film conductors embedded or encased between upper and lower layers and of a selected insulative material such as polyimide film or sheet. The sensor electrodes 18 at a tip end of the distal segment 16 are exposed through one of the insulative layers for direct contact with patient blood, when the sensor is transcutaneously placed. The distal segment 16 is joined to a proximal segment 20, the end of which terminates in conductive contact pads 22 which are also exposed through one of the insulative layers. As is known in the art, and illustrated schematically in FIG. 1, these conductive contact pads 22 are adapted for electrical connection to a suitable monitor 24 for monitoring patient condition in response to signals derived from the sensor electrodes. Further description of flexible thin film sensors of this general type may be found in copending U.S. Ser. No. 08/212,961, filed Mar. 14, 1994, now U.S. Pat. Nos. 5,391,250, entitled METHOD OF FABRICATING THIN FILM SENSORS, and U.S. Ser. Nos. 08/239,960, filed May. 9, 1994, now U.S. Pat. Nos. 5,482,473, entitled FLEX CIRCUIT CONNECTOR, which are incorporated by reference herein. In this regard, FIGS. 1–3 show connection of the sensor proximal segment 20 connected electrically to the monitor 24 by means of a connector block 26 having conductive strip elements 28 (FIG. 2) as described in U.S. Ser. No. 08/239,960 now U.S. Pat. No. 5,482,473.

In general, the sensor 12 is carried by a mounting base 30 adapted for placement onto the skin of a patient. As shown, the mounting base 30 comprises an enlarged and generally rectangular mounting pad structure defining oppositely projecting wings 32 each having an underside surface coated with a suitable pressure sensitive adhesive. A peel-off paper strip (not shown) is normally provided to cover and protect the adhesive layer, until the insertion set 10 is ready for use.

More particularly, as shown in one preferred construction in FIGS. 1–4, the mounting base 30 comprises a central housing member 34 formed from a suitable medical grade and relatively stiff or rigid plastic material such as polycarbonate or the like. This central housing member 34 is adapted to receive and support the proximal segment 20 of the sensor 12 in a position with the contact pads 22 thereon for connection to the monitor 24 by means of the connector block 26 as previously described. A locator pin 36 (FIG. 2) may be provided on the housing member 34 for reception through a port 38 formed in the sensor proximal segment 20 to insure proper mounting position of the sensor. In addition, FIG. 2 shows a square aperture 40 in the housing member 34 for seated reception of the connector block 26. The sensor proximal segment 20 is joined at a bend 42 to the distal segment 16 which protrudes downwardly through an open port 44 to terminate at a selected depth or spacing below the housing member 34.

As shown best in FIGS. 2–5, the flexible cannula 15 has a mounting flange 46 at an upper or proximal end thereof nested within a recess 48 in the housing member 34 at the port 44. The cannula mounting flange 46 has a noncircular cross sectional shape, such as a D-shaped configuration as shown, for mating unidirectional seated fit into the housing member recess 48. Accordingly, the cannula 15 is supported by the housing member 34 in a predetermined rotational orientation, to correspondingly orient the window 19 therein in a predetermined position relative to the mounting base. From the mounting flange 46, the cannula 15 protrudes through the port 44 in an angularly downward and forward direction with the distal segment 16 of the sensor 12 nested therein.

The attachment wings 32 of the mounting base 30 are formed by the opposite ends of a resilient wing member 52 (FIG. 2) having a size and shape to transversely overlie the central housing member 34. A central region of this wing member 52 has a pair of slots 54 formed thereon for pass-through reception of a downwardly projecting pair of snap-fit tabs 56 of an overlying cover plate 58. This cover plate 58 is formed from a suitable stiff or rigid material such as polycarbonate plastic, and includes additional snap-fit feet 60 for engaging and retaining the wing member 52 tightly against the underlying housing member 34, and thereby engage and retain the sensor proximal segment 20 tightly against the connector block 26.

The insertion needle 14 is adapted for slide-fit reception through circular needle ports 62 and 64 formed respectively in the cover plate 58, and through the wing member 52. As shown in FIGS. 1 and 2, the insertion needle 14 extends further through the cannula 15 alongside the sensor distal segment 16, to terminate in a sharpened tip 66 which protrudes a short distance beyond the cannula.

In accordance with a primary aspect of the invention, as shown in FIGS. 1–3, the mounting of the cannula 15 in the predetermined orientation relative to the housing member 34 results in the cannula windows or window 19 also being oriented in a predetermined manner, such as being exposed downwardly as viewed in the illustrative drawings. With this construction, the sensor distal segment 16 can be manufactured with the electrodes 18 thereon oriented for downward exposure, when the sensor is installed onto the mounting base 30 as shown. Accordingly, reliable and positive alignment of the sensor electrodes 18 with the cannula window 19 results to insure that the sensor electrodes 18 are properly exposed for direct contact with patient body fluid during use.

The insertion set 10 is installed quickly and easily by pressing the mounting base 30 onto the patient's skin. During this step, the insertion needle 14 pierces the patient's skin and carries the cannula 15 with the sensor distal segment 16 therein to the appropriate transcutaneous placement site. During insertion, the sensor distal segment 16 is supportively sandwiched between the needle 14 and a lower interior wall of the cannula 15, with the distal segment 16 projecting at least slightly beyond the window 19 to prevent inadvertent sensor dislocation from within the cannula.

When the sensor is transcutaneously placed, with the mounting base 30 seated upon the patient's skin, the insertion needle 14 can be withdrawn from the patient. During this withdrawal step, the insertion needle 14 slides from within the cannula 15 and along the sensor distal segment 16, leaving the sensor distal segment 16 with the electrodes 18 thereon at the selected insertion site in alignment with the cannula window 19. The electrodes are thus exposed to patient blood or other body fluid, resulting in signals which are coupled via the conductive contact pads 22 on the sensor proximal segment 20 to the monitor 24. The sensor 12 can thus be used over a prolonged period of time for taking blood chemistry readings, such as blood glucose readings in a diabetic patient.

FIGS. 7–12 show alternative cannula and sensor geometries for exposing sensor electrodes 18 on a sensor distal segment for direct contact with patient body fluid. For convenience, modified structures conforming in function to those previously shown and described are identified in FIGS. 7–12 by primed reference numerals.

More specifically, FIGS. 7 and 8 show a modified cannula 15' at a distal end thereof to include a modified window 19' defined by a pair of spaced-apart radial slits formed in the cannula. In this version, the sensor distal segment 16 (FIG. 11), which can be identical to the sensor shown in FIGS. 1–6, extends within the cannula 15' through the radial slits so that sensor electrodes 18 are located exteriorly of the cannula segment disposed axially between the radial slits. The sensor distal segment 16 projects through both slits, whereby the sensor terminates within the cannula 15' at a location beyond the window 19' to achieve a mechanical interlock between the cannula and sensor, to assist in preventing inadvertent sensor dislocation.

FIGS. 9, 10 and 12 show a further modified form wherein a cannula 15" has a window 19" defined by spaced radial slits, but wherein the cannula material between these slits is further cut in the axial direction to define a pair of flaps 62. In this version, the sensor has a modified distal segment 16' with electrodes 18 thereon (FIG. 12), but including an enlarged end tab 64. The sensor distal segment 16' is installed with the electrodes 18 exposed through the window 19", with the flaps 62 located radially inboard thereof, and with the end tab 64 extending beyond the flaps 62 within the cannula 15" to achieve a mechanical interlock which prevents sensor dislocation. In both of the embodiments of FIGS. 7–12, the cannula window is normally oriented downwardly as described previously with respect to FIGS. 1–6, to issue proper alignment with the sensor electrodes 18 when the insertion set is assembled. The insertion needle 14 (not shown in FIGS. 7–12) supports the sensor against the lower interior wall of the cannula during sensor placement on a patient, as previously described.

The transcutaneous sensor insertion set of the present invention thus provides a relatively simple device for quickly and easily placing a flexible thin film electrochemical sensor at a selected position within a patient. The device is assembled quickly and easily, with positive component alignment and orientation being assured.

A variety of modifications and improvements to the transubcutaneous sensor insertion set of the present invention will be apparent to those skilled in the art. As an example, the resilient cannula may be used to deliver a medication to or otherwise withdraw fluid from the patient, in addition to the functions of supporting and protecting the sensor. Accordingly, no limitation on the invention is intended by way of the foregoing description and accompanying drawings, except as set forth in the appended claims.

What is claimed is:

1. A transcutaneous sensor insertion set, comprising:

a mounting base adapted for mounting onto a patient's skin;

a flexible sensor having a proximal segment carried by said mounting base, and a distal segment protruding from said mounting base and having at least one sensor electrode thereon;

a hollow cannula having a window formed therein;

cooperative mount means on said mounting base and said cannula for supporting said cannula from said mounting base to protrude therefrom with said sensor distal segment received therein and with said cannula in a predetermined orientation relative to said mounting base for positioning said window formed in said cannula generally in alignment with said at least one sensor electrode; and an insertion needle carried by said mounting base to protrude therefrom through said cannula whereby said sensor distal segment is interposed and supported between said needle and an interior wall surface of said cannula, said insertion needle being slidably withdrawable from said mounting base and said cannula to leave said sensor distal segment within said cannula.

2. The transcutaneous sensor inseration set of claim 1 wherein said cooperative mount means comprises a mounting flange of noncircular cross sectional shape on said cannula and a matingly shaped recess formed in said mounting base for seated reception of said mounting flange.

3. The transcutaneous sensor insertion set of claim 1 further including means for securing said sensor distal segment in position relative to said cannula.

4. The transcutaneous sensor insertion set of claim 1 wherein said sensor distal segment has a length to extend within said cannula to a position axially beyond said window.

5. The transcutaneous sensor insertion set of claim 1 wherein said window is formed by a pair of axially spaced, radially extending slits formed in said cannula, said sensor distal segment extending through said slits to expose a portion of said sensor distal segment to the exterior of said cannula, said exposed portion having said at least one electrode thereon.

6. The transcutaneous sensor insertion set of claim 5 wherein said sensor distal segment includes an enlarged tab at a free end thereof, said tab being positioned within said cannula at a location axially beyond said window.

7. The transcutaneous sensor insertion set of claims 1 wherein said sensor is a flexible thin film sensor.

8. The transcutaneous sensor insertion set of claim 1 wherein said sensor is an electrochemical sensor.

9. The transcutaneous sensor insertion set of claim 1 wherein said sensor is a glucose sensor.

10. The transcutaneous sensor insertion set of claim 1 wherein said insertion needle extends through an open port formed in said mounting base, said insertion needle being positioned to pierce a patient's skin to carry said cannula with said sensor distal segment therein to an insertion position within the patient upon placement of said mounting base onto the patient's skin, said insertion needle being slidably withdrawable from the patient's skin and said mounting base to leave said cannula with said sensor distal segment therein at the insertion position.

11. The transcutaneous sensor insertion set of claim 1 wherein said mounting base comprises a central housing member for receiving and supporting said cannula and for receiving and supporting said sensor with said proximal segment thereon and with said distal segment disposed angularly relative to said proximal segment to extend into said cannula, a wing member overlying said central housing member and defining oppositely projecting wings for removable attachment to a patient's skin, and a cover plate overlying a portion of said wing member and including attachment means for connection to said central housing member with said portion of said wing member clamped between said cover plate and central housing member.

12. The transcutaneous sensor insertion set of claim 11 wherein said attachment means comprises snap-fit tabs formed on said cover plate.

13. The transcutaneous sensor insertion set of claim 1 wherein said mounting base further includes an electrical connector element conductively connected to said sensor proximal segment.

14. A transcutaneous sensor insertion set, comprising:

a mounting base adapted for placement onto a patient's skin and having an open part formed therein;

a flexible sensor having a proximal segment carried by said mounting base, a distal segment protruding downwardly from said mounting base and having a tip end with at least one sensor electrode thereon;

a hollow cannula having one end supported by said mounting base and protruding therefrom with said sensor distal segment therein;

cooperative mount means on said cannula and said mounting base for orienting said cannula in a predetermined orientation relative to said mounting base, said cannula having at least one window formed therein for exposing said sensor electrode to patient body fluid; and an insertion needle slidably receivable through an open port formed in said mounting base to extend through said cannula whereby said sensor distal segment is supported between said needle and an interior wall surface of said cannula;

said insertion needle being positioned to pierce a patient's skin to carry said cannula and said sensor distal segment therein to an insertion position within the patient upon placement of said mounting base onto the patient's skin, said insertion needle being slidably withdrawable from the patient's skin and said mounting base to leave said cannula with said sensor distal segment therein at the insertion position.

15. The transcutaneous sensor insertion set of claim 14 wherein said mounting base supports said sensor proximal segment in angular relation to said cannula with said sensor distal segment therein.

16. The transcutaneous sensor insertion set of claim 14 further including means for securing said sensor distal segment in position relative to said cannula.

17. The transcutaneous sensor insertion set of claim 14 wherein said mounting base comprises a central housing member for receiving and supporting said cannula and for receiving and supporting said sensor with said proximal segment thereon and with said distal segment disposed angularly relative to said proximal segment to extend into said cannula, a wing member overlying said central housing member and defining oppositely projecting wings for removable attachment to a patient's skin, and a cover plate overlying a portion of said wing member and including attachment means for connection to said central housing member with said portion of said wing member clamped between said cover plate and central housing member.

18. The transcutaneous sensor insertion set of claim 17 wherein said attachment means comprises snap-fit tabs formed on said cover plate.

* * * * *